(12) United States Patent
Iwasaki et al.

(10) Patent No.: US 8,012,708 B2
(45) Date of Patent: *Sep. 6, 2011

(54) METHOD FOR DETERMINATION OF ALLERGEN IN ENVIRONMENT AND KIT FOR SIMPLE QUANTIFICATION OF ALLERGEN

(75) Inventors: Aki Iwasaki, Yokohama (JP); Koji Suzuki, Yokohama (JP)

(73) Assignee: Japan Science and Technology Agency, Saitama (JP)

( * ) Notice: Subject to any disclaimer, the term of this patent is extended or adjusted under 35 U.S.C. 154(b) by 397 days.

This patent is subject to a terminal disclaimer.

(21) Appl. No.: 11/922,106

(22) PCT Filed: Jun. 16, 2006

(86) PCT No.: PCT/JP2006/312184
§ 371 (c)(1),
(2), (4) Date: Aug. 7, 2008

(87) PCT Pub. No.: WO2006/135071
PCT Pub. Date: Dec. 21, 2006

(65) Prior Publication Data
US 2009/0203058 A1     Aug. 13, 2009

(30) Foreign Application Priority Data

Jun. 17, 2005 (JP) ................................. 2005-177814

(51) Int. Cl.
*C12Q 1/37* (2006.01)
(52) U.S. Cl. ........................................................ 435/23
(58) Field of Classification Search ......................... None
See application file for complete search history.

(56) References Cited

U.S. PATENT DOCUMENTS 5,667,979 A     9/1997  Berrens

FOREIGN PATENT DOCUMENTS

| EP | 1712637 A1 | 10/2006 |
|---|---|---|
| JP | 3-259096 A | 11/1991 |
| JP | 05-207892 A | 8/1993 |
| JP | 06-034518 A | 2/1994 |
| JP | 09-087298 A | 3/1997 |
| JP | 11-014511 A | 1/1999 |
| JP | 2000-035428 A | 2/2000 |
| WO | WO-2005/059166 A1 | 6/2005 |

OTHER PUBLICATIONS

Ando et al. "Trypsin-like protease of mites: purification and characterization of trypsin-like protease from mite faecal ectract *Dermatophagoides farinae*. Relationship between trypsin-like protease and Der f III", Clinical and Experimental Allergy, 1993, 23:777-784.*
Sercombe et al. "Evaluation of home allergen sampling devices", Allergy, 2005, 60:515-520.*
Aki Honda et al., Dai 66 Kai Bunseki Kagaku Toronkai Koen Yoshishu, Apr. 30, 2005, p. 158.
Lubertus Berrens, "Estimation of the Allergen Content of House Dust Samples by Enzymatic Assay," Environmental Research, Academic Press, vol. 56, No. 1, pp. 68-77 (1991).
O. Schulz, et al., "A sensitive fluorescent assay for measuring the cysteine protease activity of Der p 1, a major allergen from the dust mite *Dermatophagoides pteronyssinus*," MP. Molecular Pathology, BMJ Publishing Group, vol. 51, No. 4, pp. 222-224, (1998).
Supplementary European Search Report dated Jun. 24, 2009.

* cited by examiner

*Primary Examiner* — Karen Carlson
*Assistant Examiner* — Bin Shen
(74) *Attorney, Agent, or Firm* — Birch, Stewart, Kolasch & Birch, LLP

(57) ABSTRACT

A simple method for measuring allergens is disclosed, by which the amount of environmental allergens can be measured simply without using an anti-allergen antibody. In the method for measuring an environmental biological allergen (s), a solution containing a substrate of a protease which the allergen(s) has (have) is brought into contact with a test sample collected by using an adhesive sheet, which substrate gives a visible color change as a result of an enzyme reaction; and measuring the protease activity in the test sample using the color change of the substrate solution as an index, thereby measuring the biological allergen(s).

12 Claims, 2 Drawing Sheets

METHOD FOR DETERMINATION OF ALLERGEN IN ENVIRONMENT AND KIT FOR SIMPLE QUANTIFICATION OF ALLERGEN

TECHNICAL FIELD

The present invention relates to a method for measuring environmental allergens, and to a simple allergen-quantification kit.

BACKGROUND ART

It is well-known that pollen contained in atmosphere, mites contained in carpets and futon, and the like serve as allergens to cause allergic diseases such as pollinosis, atopy and asthma. It is important for those with allergic diathesis to avoid contact with these allergens in order to prevent onset of allergies.

Measurements of allergens have been conventionally carried out by immunoassays using the antibodies corresponding to the allergens to be measured (Patent Literatures 1 to 5 below).

However, antibodies, especially monoclonal antibodies used for increasing the measurement accuracy, are expensive.

On the other hand, it is known that there are environmental allergens originated from pollen, mites, molds, insects and the like, which have a protease activity. For example, it is known that cedar pollen (Non-patent Literature 1), ragweed pollen (Non-patent Literature 2), mesquite pollen (Non-patent Literature 3), *Aspergillus fumigatus* (Non-patent Literature 4) which is a kind of molds, allergen from *Periplaneta americana* (Non-patent Literature 5) and mites (*Dermatophagoides farinae* and *pteronyssinus*) (Non-patent Literatures 6 to 13) have a protease activity. However, these references do not disclose or suggest to measure the allergens utilizing the protease activity, and do not disclose or suggest that there is a quantitative relationship between the protease activity and the amount of allergen. Further, in these references, the protease activities are measured after extracting, concentrating and/or purifying the allergens, and they do not disclose or suggest that environmental allergens may be simply measured as they are without these pretreatments.

Patent Literature 1: Japanese Laid-open Patent Application (Kokai) No. 9-87298
Patent Literature 2: Japanese Laid-open Patent Application (Kokai) No. 5-207892
Patent Literature 3: Japanese Laid-open Patent Application (Kokai) No. 11-14511
Patent Literature 4: Japanese Laid-open Patent Application (Kokai) No. 2000-35428
Patent Literature 5: Japanese Laid-open Patent Application (Kokai) No. 6-34518
Non-patent Literature 1: J Agric Food Chem. 2002 Jun. 5; 50(12):3540-3. Isolation and characterization of aminopeptidase (Jc-peptidase) from Japanese cedar pollen (*Cryptomeria japonica*). Noguchi Y, Nagata H, Koganei H, Kodera Y, Hiroto M, Nishimura H, Inada Y, Matsushima A.
Non-patent Literature 2: Phytochemistry. 1998 February; 47(4):593-8. Ragweed pollen proteolytic enzymes: possible roles in allergies and asthma. Bagarozzi D A Jr, Travis J.
Non-patent Literature 3: Am J Respir Cell Mol Biol. 1995 April; 12(4):441-8. Isolation and properties of an angiotensin II-cleaving peptidase from mesquite pollen. Matheson N, Schmidt J, Travis J.
Non-patent Literature 4: J Investig Allergol Clin Immunol. 2002; 12(4):257-62. Serine proteinases with gelatinolytic activity in an *Aspergillus fumigatus* allergenic extract. Iraneta S G, Duschak V G, Rodriguez S M, Alonso A.
Non-patent Literature 5: J Investig Allergol Clin Immunol. 1999 July-August; 9(4):235-40. Proteinase and gelatinolytic activities of house dust mite and cockroach extracts. Iraneta S G, Duschak V G, Rodriguez S M, Seoane M A, Albonico J F, Alonso A.
Non-patent Literature 6: Ando T, Ino Y, Haida M, Honma R, Maeda H, Yamakawa H, Iwaki M, Okudaira H. Isolation of cysteine protease in the crude mite extract, *Dermatophagoides farinae*. Int Arch Allergy Appl Immunol. 1991; 96(3):199-205.
Non-patent Literature 7: Ando T, Homma R, Ino Y, Ito G, Miyahara A, Yamakawa H, Iwaki M, Okumura Y, Suko M, Haida M, et al. Is a trypsin-like protease of mites a Der f III allergen? Arerugi. 1992 June; 41(6):704-7.
Non-patent Literature 8: Ando T, Homrnma R, Ino Y, Ito G, Miyahara A, Yanagihara T, Kimura H, Ikeda S, Yamakawa H, Iwaki M, et al. Trypsin-like protease of mites: purification and characterization of nypsin-like protease from mite faecal extract *Dermatophagoides farinae*. Relationship between trypsin-like protease and Der fIII. Clin Exp Allergy. 1993 September; 23(9):777-84.
Non-patent Literature 9: King C, Simpson R J, Moritz R L, Reed G E, Thompson P J, Stewart G A. The isolation and characterization of a novel collagenolytic serine protease allergen (Der p 9) from the dust mite *Dermatophagoides pteronyssinus*. J Allergy Clin Immunol. 1996 October; 98(4):739-47.
Non-patent Literature 10: Schulz 0, Sewell H F, Shakib F. Related Articles, Links A sensitive fluorescent assay for measuring the cysteine protease activity of Der p 1, a major allergen from the dust mite *Dermatophagoides pteronyssinus*. Mol Pathol. 1998 August; 51(4):222-4.
Non-patent Literature 11: Yasueda H, Mita H, Akiyama K, Shida T, Ando T, Sugiyama S, Yamakawa H. Allergens from Dermatophagoides mites with chymotryptic activity. Clin Exp Allergy. 1993 May; 23(5):384-90.
Non-patent Literature 12: Heymann P W, Chapman M D, Aalberse R C, Fox J W, Platts-Mills T A. Antigenic and structural analysis of group II allergens (Der f II and Der p II) from house dust mites (*Dermatophagoides* spp). J Allergy Clin Immunol. 1989 June; 83(6):1055-67.
Non-patent Literature 13: Stewart G A, Ward L D, Simpson R J, Thompson P J. Related Articles, Links The group III allergen from the house dust mite *Dermatophagoides pteronyssinus* is a trypsin-like enzyme. Immunology. 1992 January; 75(1):29-35.

DISCLOSURE OF THE INVENTION

Problems which the Invention Tries to Solve

An object of the present invention is to provide a method for measuring allergens, by which environmental allergens may be measured simply without using an anti-allergen antibody, and to provide a simple allergen-quantification kit for carrying out the method.

Means for Solving the Problems

As a result of intensive study, the present inventors discovered that environmental biological allergens may be very simply measured by collecting the biological allergens such as mites and pollen with an adhesive tape; and measuring the protease activity which the biological allergens have using a substrate which gives a visible color change as a result of an enzyme reaction; even without a pretreatment such as extraction or concentration of the allergens, and without using an instrument or apparatus for detection, and developed a kit for carrying out the method, thereby completing the present invention.

That is, the present invention provides a method for measuring an environmental biological allergen(s), characterized in that the method comprises the steps of contacting a solution containing a substrate of a protease which the allergen(s) has (have) with a test sample collected by using an adhesive sheet, the substrate giving a visible color change as a result of an enzyme reaction; and measuring the protease activity in the test sample using the color change of the substrate solution as an index, thereby measuring the biological allergen(s). The present invention also provides a simple allergen-quantification kit for carrying out the method according to the present invention, the kit comprising a solution of the substrate of the protease, or a porous matrix impregnated with the solution; and a tape for collecting the test sample.

Effects of the Invention

By the present invention, a method for measuring allergens, by which environmental biological allergens may be measured simply without using an anti-allergen antibody, as well as a simple allergen-quantification kit for carrying out the method, was first provided. Since the method of the present invention does not use an anti-allergen antibody, it may be carried out inexpensively. Further, with the method and kit of the present invention, since the method may be carried out without a pretreatment of the allergen, using a test sample as it is collected with an adhesive tape such as a commercially available adhesive sheet, and since the detection can be attained merely visually observing the change in color without using a special instrument or apparatus, the method is extremely simple and may be carried out without a skill. Still further, since the kit according to the present invention is easily portable, measurement of allergens may be carried out in situ at the place such as home or school at which the allergens are desired to be measured. Therefore, it is expected that the present invention will greatly contribute to the prevention of allergic diseases such as atopy and pollinosis.

BEST MODE FOR CARRYING OUT THE INVENTION

Figure 1:
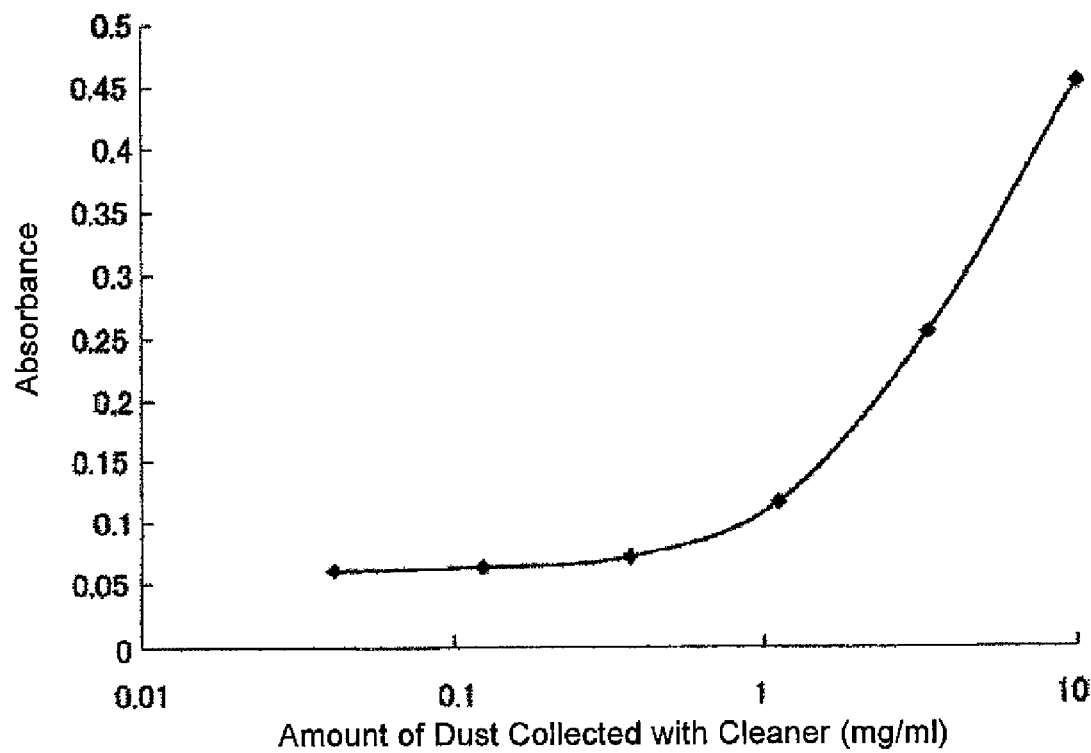
FIG. 1 shows the relationship between the amount of dust collected with a cleaner and absorbance, which was measured in Reference Example of the present invention.

The measuring objects to be measured by the method of the present invention are environmental biological allergens. Here, "environment" means atmosphere and room air, as well as insides and outsides of floors, walls, windows, window frames, floor coverings (carpets, rugs, tatami mats, mats, straw mats and the like), beddings (futon, blankets, pillows, mattress and the like), fiber products such as fabrics, furnitures (chairs, sofas and the like), dust, house dust and the like, which may be a source of allergens to the room air. "Biological allergens" are living organisms per se and substances produced by living organisms, which cause allergies, such as pollens; bodies, feces, dead bodies and debris of mites and insects; molds and spores thereof; and the like.

In the method of the present invention, an allergens) is (are) measured by measuring the protease activity thereof. Therefore, the measuring object(s) of the method of the present invention and of the simple allergen-quantification kit using the method is (are) an allergen(s) having protease activity. Preferred examples thereof include pollens, especially cedar pollen and mites (bodies, feces, dead bodies and debris). However, the allergens are not restricted thereto, and molds may also be the measuring objects.

In the method of the present invention, the protease activity of the above-described environmental biological allergen(s) is measured. Although the fact per se that environmental biological allergens have protease activity is known, it was not known that there is a quantitative relationship between protease activity and the amount of an allergen, and that the allergen may be measured by measuring the protease activity. Further, surprisingly, as will be described concretely in Reference Examples and Examples below, it was discovered by the present inventors that the protease activity of environmental biological allergens may be measured without any pretreatment such as extraction, concentration or purification of the allergens. Thus, in a preferred mode of the present invention, the environmental biological allergen(s) is (are) collected using an adhesive sheet such as a commercially available adhesive tape, and subjected to the measurement as it (they) is (are) in the state of being adhered to the adhesive sheet without any pretreatment, so that the method is extremely simple. In this case, the measurement can be performed at room temperature, and to perform the measurement at room temperature is simple and preferred. The term "measure" includes both quantification and detection.

In the method of the present invention, for measuring the protease activity, a substrate which gives a visible color change as a result of an enzyme reaction is used as the substrate of the protease. By this, a special instrument or apparatus is not necessary for the measurement, and the measurement can be easily attained by visual observation, which is extremely simple. Preferred examples of such a substrate will be described later.

Since the substrate specificity of protease differs depending on the type of the allergen, the substrate with which the protease of the allergen to be measured reacts is selected and used. This selection may be carried out merely by a routine check test. Further, protease inhibitors are also known. By making a protease inhibitor which inhibits the protease activity of a particular allergen coexist with the substrate used for the measurement, the protease activity of the particular allergen is eliminated, and the protease activity of the target allergen may be selectively measured. Examples of the protease inhibitors include p-methacrylbenzoic acid, diisopropyl fluorophosphate, tosylphenylalanyl chloromethyl ketone, subtilisin inhibitor, leupeptin, antipain, pepstatin and epoxy succinic acid derivatives. Thus, by appropriately selecting the substrate, and by making an inhibitor(s) against the protease of the allergen(s) which is desired to be excluded from the measurement, the type of the allergens to be measured may be considerably narrowed down.

The present inventors further invented pigments whose color is changed by the enzyme reaction by protease. That is, the present inventors discovered that when a protease acts on a colored compound which is a pigment having at least one amino group, in which an amino acid(s) and/or oligopeptide(s) is (are) bound to one or more of the at least one amino group through an amide bond(s), the amide bond(s) is (are) cleaved, that results in color change of the compound. The term "color change" herein means that both colors of the compound before and after the enzyme reaction can be visually seen, and the color change is discernible by visual observation. Color change may be more simply observed than fluorescence which requires excitation light, and even a slight change is more readily discernible than coloring (colorless compound is colored), so that observation of color change is advantageous. Preferred examples of the colored pigment include the pigments having an amino group(s) in a conjugated system, such as cresyl violet, Safranin O, methylene violet 3RAX, Nile blue A, Darrow red, Azure A, Azure C, Brilliant cresyl blue, rhodamine 123 and thionine. Especially preferred examples include, but not limited to, cresyl violet Safranin O and methylene violet 3RAX, having the following chemical structures;

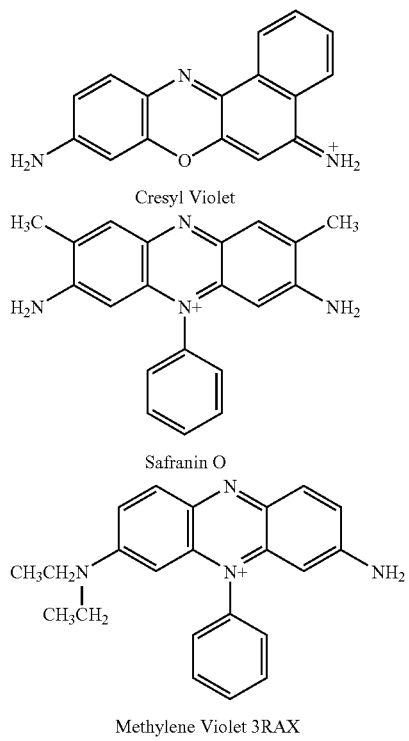

Cresyl Violet

Safranin O

Methylene Violet 3RAX

In cases where the colored pigment has a plurality of amino groups as cresyl violet, it is sufficient if at least one of the amino groups is amidated. The amino acid to be subjected to amidation may be only one amino acid molecule or may be an oligopeptide (preferably one containing 2 to about 10 amino acids). An amino group of an amino acid or the amino group of the N-terminal of an oligopeptide may be protected with a protective group such as Boc group (t-butyloxycarbonyl group), and the amino acids and oligopeptides whose amino group(s) is (are) protected are also included in "amino acid" and "oligopeptide" as used in the present description and claims. The type of the amino acid and oligopeptide may appropriately be selected depending on the protease as described above. For example, for the measurement of *Dermatophagoides farinae* extract or *Dermatophagoides pteronyssinus* extract P, which is a mite antigen, those wherein one molecule of leucine, methionine or lysine is amidated are preferred, especially those wherein one or two amino groups of cresyl violet is bound to leucine by an amide bond(s) are preferred. It should be noted that the activity of cleaving the amide bond through which one molecule of amino acid is bound is endopeptidase activity, and it was first discovered by the present inventors that allergens such as mite antigen have endopeptidase activity. Further, those employing methylene violet 3RAX is used as colored pigment, and a Boc-amino acid or Boc-Val-Leu-Lys (the side of lysine is bound to the colored pigment, Boc means t-butyloxycarbonyl) is bound (that is, Boc-amino acid-3RAX and Boc-Val-Leu-Lys-3RAX (wherein in these formulae, 3RAX represents methylene violet 3RAX) may also preferably be employed especially for the measurement of mite antigen.

The amide bond between the colored pigment and the amino acid may be attained by reacting the colored pigment molecule and the amino acid whose amino group is protected with Boc using as a condensation agent carbonyl diimidazole at room temperature for 1 day in methylene chloride or DMF, and after formation of the amide bond, deprotecting the amino group by trifluoroacetic acid. Detailed methods are described in Reference Examples and Examples below. Oligopeptides may also be subjected to the formation of amide bond by the similar method.

The above-described substrates which bring about color change may preferably be used in the state of solutions. As the solvent, water and aqueous buffer solutions may preferably be used. Although the concentration of the substrate is appropriately selected depending on the type of the substrate used and the range of the amount of the expected allergen(s), the concentration is usually about 1 μM to about 50 mM, preferably about 5 μM to about 20 μM, although the concentration is not restricted thereto.

The measurement may be performed by bringing an adhesive sheet into contact with a floor(s), wall(s), window(s), window frame(s), floor covering(s) (such as carpets, rugs, tatami mats, mats and straw mats), bedding(s) (such as futon, blankets, pillows and mattress), fiber products such as fabrics, and/or furniture(s) (such as chairs and sofas); contacting the adhesive sheet with a substrate solution; and observing the change in fluorescence or absorbance of the substrate solution, preferably by visually observing the color change of the substrate solution. In this case, it is simple and preferred to contact the adhesive sheet which was brought into contact with the floor(s), wall(s), window(s), window frame(s), floor covering(s), bedding(s), fiber products and/or furniture(s) with the substrate solution without performing any pretreatment. Further, in this case, the contact with the substrate solution can be performed at room temperature, and to perform the contact at room temperature is simple and preferred. The contact between the adhesive sheet and the substrate solution may be carried out by immersing the adhesive sheet in the substrate solution contained in a vessel, or the adhesive sheet may be brought into contact with a porous matrix impregnated with the substrate solution. In the latter case, as the porous matrix, spongiform polymers, and gels such as agar gel, gelatin gel, polyacrylamide gel may be used.

As the adhesive sheet, commercially available adhesive tapes (Cellophane tape (registered trademark) produced by Nichiban) and the like may preferably be used. As the adhesive sheet, in order to enhance the elution of the collected fine dust, those adhesive sheets in which an adhesive having a high water solubility may preferably be used. Such a water-soluble adhesive may be one employing an acrylic polymer as the base polymer, and examples thereof include, but not limited to, carboxylic acids such as itaconic acid, maleic acid, acrylic acids, methacrylic acid and derivatives thereof; polymers of a salt or ester of these carboxylic acids; and acrylic polymers such as polyacrylamide. Further, to attain effective collection of fine dust alone, an adhesive sheet having irregularities on the adhesive surface may also be used.

EXAMPLES

The present invention will now be described more concretely by way of Reference Examples and Examples thereof. It should be noted, however, the present invention is not limited to the Reference Examples and Examples below.

Reference Example 1

Quantification of Mite Antigen in House Dust by Visual Observation or Measurement of Absorbance (1) Materials
House Dust (dust collected with a cleaner)
Protease Substrate (Bz-DL-Arg-pNA, HCl) (Bz: benzoyl, pNA: paranitroanilide, produced by PEPTIDE INSTITUTE INC)
(2) Methods and Results
The dust collected with a cleaner was suspended in phosphate buffer to a concentration of 10 mg/ml and the obtained suspension was filtered through a filter having a pore size of 1 µm. The obtained filtrate was 3-fold serially diluted 6 times. Each dilution in an amount of 180 µL was mixed with 20 µL of the substrate dissolved in DMSO to a concentration of 10 mM, and the mixture was incubated at 37° C. overnight. The colored plate was scanned from the downside with a scanner. As a result, coloring in yellow was observed in the wells containing a sample with a high concentration. The absorbance at 405 nm was measured with a plate reader. The results are shown in FIG. 1. This curve is approximated to the following equation taking the amount of the dust collected with the cleaner as x and talking the absorbance as y:

$$y=((A-D)/(1+(x/C)^B))+D$$

A=0.061, B=1.398, C=5.059, D=0.575
From this curve, it can be seen that mite antigen in house dust, at least within the range between about 1 mg/ml to 10 mg/ml, may be quantified by the method of this Example.

Reference Example 2

(1) Synthesis of Colored Compound Which Changes Color by Enzyme Cleavage

Substrates which change their color by cleavage by an enzyme were synthesized. To each of the amino groups of cresyl violet, Safranin O and methylene violet 3RAX, leucine or methionine was bound through an amide bond(s). That is, the pigment molecules (final concentration: 0.1M), the amino acid (final concentration: 0.2M) whose amino group was protected with Boc, and carbonyl diimidazole (final concentration 0.1M) as a condensing agent, were reacted at room temperature for one day in methylene chloride or DMF, thereby forming an amide bond(s). After the reaction, the amino group(s) was (were) deprotected using trifluoroacetic acid (50%)/methylene chloride (50%).

Cresyl violet has two amino groups. By the above-described synthesis process, the compound (yellow, maximum absorption wavelength: 440 nm) in which both of the amino groups were bound to the amino acid through amide bonds, and the compound (orange, 490 nm) in which only one of the amino groups was bound to the amino acid through an amide bond, were isolated. The absorption wavelength of each compound was measured with a plate reader (SPECTRA Max).

Figure 2:
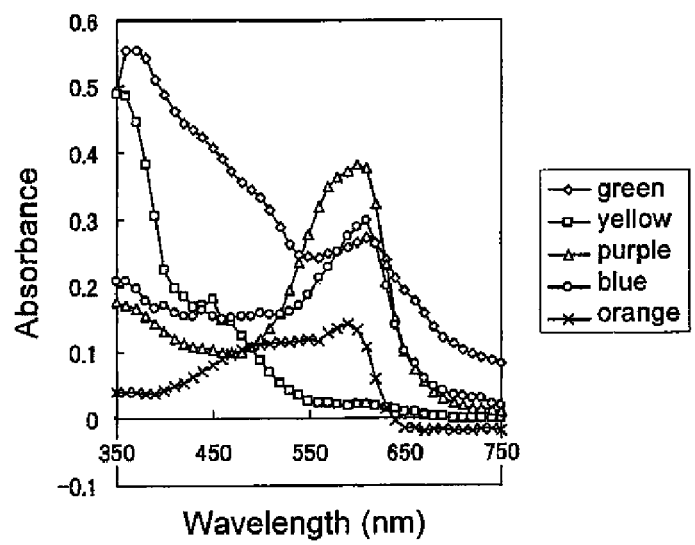
FIG. 2 shows spectra of the starting substance and reaction mixture before, after and during the enzyme reaction, respectively, the enzyme reaction being the reaction resulted by allowing aminopeptidase M to act on cresyl violet to which leucine molecule(s) was (were) bound through an amide bond (s).

An experiment to cleave the amino bond(s) in the compounds between leucine and cresyl violet was carried out by adding aminopeptidase M. That is, to 50 µL of a solution of aminopeptidase M, an enzyme which cleaves off the N-terminal amino acid bound through amide bond, diluted with PBS as appropriate, 5 µL of the substrate dissolved in ethanol to a concentration of about 10 mM was added. After leaving the mixture to stand for 30 minutes, absorption spectrum was measured using a 96-well plate. As a result, the absorption spectrum of the substrate in which only one of the amino groups contributed to the formation of amide bond changed from orange (maximum absorption wavelength: 490 nm) to violet (maximum absorption wavelength: 590 nm) upon digestion with the enzyme, and the absorption spectrum of the substrate in which both amino groups contributed to the formation of amide bond changed from yellow (maximum absorption wavelength: 450 nm) to violet (maximum absorption wavelength: 590 nm) via green and blue. Mass spectrometry revealed that the blue substance was the compound in which one leucine molecule was bound to cresyl violet. The violet absorption spectrum finally attained by the enzyme digestion was completely coincide with that of cresyl violet per se, and it was also confirmed by thin layer chromatography that the substance was cresyl violet itself. The reason why the compound in which cresyl violet is bound with one leucine molecule gives two different colors of blue and orange is that the molecular structure of cresyl violet is not symmetric, and the absorption spectrum differs depending on which amino group participates in the formation of the amide bond. The respective absorption spectra are shown in FIG. 2. It was confirmed that similar color change occurred when methionine or lysine was used in place of leucine.

Figure 3:
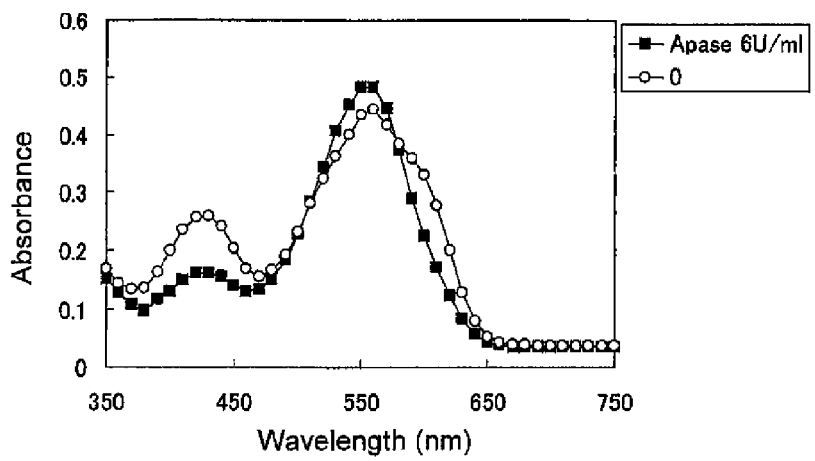
FIG. 3 shows spectra of the starting substance and reaction mixture before and after the enzyme reaction, respectively, the enzyme reaction being the reaction resulted by allowing amide peptidase M to act on methylene violet to which leucine was bound through amide bond.
Figure 4:
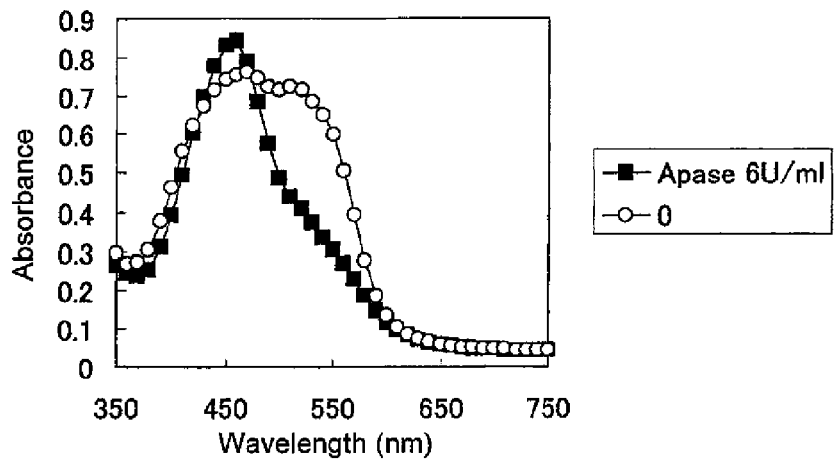
FIG. 4 shows spectra of the starting substance and reaction mixture before and after the enzyme reaction, respectively, the enzyme reaction being the reaction resulted by allowing aminopeptidase M to act on Safranin-O to which leucine molecule(s) was (were) bound through an amide bond(s).

Methylene violet 3RAX has one amino group. When the amino group contributes to the formation of amide bond with an amino acid, its color was light violet (maximum absorption wavelengths; 550 nm and 590 nm), and upon digestion with aminopeptidase M, its color changed to bright pink (maximum absorption wavelength: 550 nm). The absorption spectrum after digestion was completely coincide with that of methylene violet 3RAX. The manner of spectrum change of the binding product of methylene violet 3RAX with leucine through amide bond, upon digestion with aminopeptidase M, is shown in FIG. 3. In FIG. 3 and in FIG. 4 described below, the term "Apase" means aminopeptidase M. The binding product of Safranin O with leucine through amide bonds has two amino groups, and binding product of this compound with leucine showed red color. Upon digestion with aminopeptidase M, it colored in orange. The absorption spectrum after the digestion was completely coincide with that of Safranin O. The manner of spectrum change of the binding product of Safranin O with leucine through amide bonds, upon digestion with aminopeptidase M, is shown in FIG. 4.

(2) Quantification of Mite Antigen with Synthesized Colored Compound

It was confirmed that the binding product (CV-Leu) of cresyl violet with leucine through amide bond changed its color depending on the amount of mite antigen in house dust. That is, the samples a to g shown in Table 1 were checked for the amount of mite antigen therein using a commercially available ELISA kit for measuring indoor allergens in accordance with the package insert. To the samples a to g, CV-Leu was added and the resulting mixtures were left to stand overnight. As a result, the samples a and b colored in violet and were shown to contain a large amount of mite antigen. These results agreed with the results of ELISA. Thus, it was proved that mite antigen can be measured using CV-Leu as a substrate based on the color change thereof.

TABLE 1

|   | Derf1 | Derp1 | Der2 | Total |
|---|---|---|---|---|
| a | 2367 | 20.6 | 60 | 2447.6 |
| b | 8367 | 171.8 | 202.8 | 8741.6 |
| c | 1567 | 18.4 | 53.8 | 1639.2 |
| d | 1831 | — | 18.6 | 1849.6 |
| e | 15.31 | — | — | 15.31 |
| f | 1199 | 17.9 | 32.2 | 1249.1 |
| g | 725 | 9.7 | 20.4 | 755.1 |

Example 1

Preparation of Kit (1) Synthesis of Colored Compound

A colored compound was prepared as follows in PEPTIDE INSTITUTE INC. First, methylene violet 3RAX was condensed with Boc-Lys(Z)-OH by the active ester method to prepare Boc-Lys(Z)-3RAX. After removing the Boc group by TFA, the product was condensed with Boc-Leu-OH by the carbodiimide-additive method to obtain Boc-Leu-Lys(Z)-3RAX. After removing the Boc group again by TFA, the product was condensed with Boc-Val-OH by the carbodiimide-additive method to obtain Boc-Val-Leu-Lys(Z)-3RAX. Finally, the Z group was removed by catalytic reduction, and the resulting product was purified by reverse phase HPLC to obtain Boc-Val-Leu-Lys-3RAX.

(2) Methods and Results

As the house dust, fine dust obtained by removing hairs and the like from the dust collected with cleaners in houses No. 1 to No. 6 was used. The fine dust was collected using adhesive sheets (Cellophane tape produced by Nichiban) each sizing 1.5 cm×1.5 cm. As a negative control, a sheet with which the house dust was not collected was also included (Blk). The amount of the mite antigen contained in each sample was measured by ELISA of Indoor, and the results are shown below in terms of the total amount of Der1f, Der2f and Derp.

TABLE 2

| Sample | ELISA Total Amount of Antigens (ng/ml) | KPS2003 Absorbance 550 nm |
|---|---|---|
| 1 | 2447.6 ± 59 | 0.6366 |
| 2 | 8741.6 ± 343.6 | 0.7256 |
| 3 | 1849.6 ± 50.5 | 0.5717 |

TABLE 2-continued

| Sample | ELISA Total Amount of Antigens (ng/ml) | KPS2003 Absorbance 550 nm |
|---|---|---|
| 4 | 15.3 ± 5.9 | 0.5081 |
| 5 | 1249.1 ± 96.1 | 0.5669 |
| 6 | 755.1 ± 18.1 | 0.5467 |
| Blk | 0 | 0.505 |

As the substrate, the above-described Boc-Val-Leu-Lys-3RAX was used. The substrate was dissolved in PBS supplemented with 1% CHAPS (trade name, ampholytic surfactant produced by Dojindo Laboratories) to a final concentration of 10 μM, and 2 ml of the obtained solution was placed in a transparent plastic case. The adhesive sheet with which the house dust was collected was immersed in the solution at room temperature for 5 minutes, and the color change was observed. As a result, with Sample No. 2, the color changed to deep pink, with Sample No. 1, the color changed to intermediate pink, and with Sample Nos. 3, 5 and 6, the color was slightly pinkish violet. With the blank and Sample No. 4, the color remained unchanged from violet which was the color of the substrate.

Reference Example 3

Change in Absorption Spectrum of Colored Compound Boc-Val-Leu-Lys-3RAX

Figure 5:
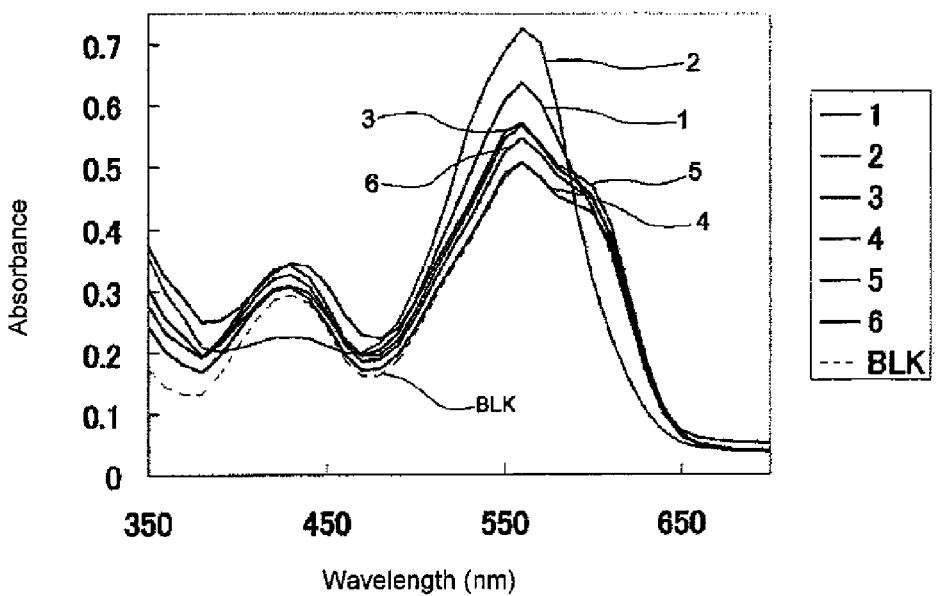
FIG. 5 shows absorption spectra of reaction mixtures obtained by mixing a colored compound Boc-Val-Leu-Lys-3 RAX prepared in an Example of the present invention with each of dilutions of house dust.

The house dust obtained in Example 1 was added to 1% CHAPS-containing PBS to a concentration of 5 mg/ml, and 50 μl of the supernatant of the resulting mixture was mixed with a 100 μM solution of the above-described substrate. The absorption spectrum at 5 minutes after the mixing is shown in FIG. 5.

INDUSTRIAL AVAILABILITY

The method and the kit according to the present invention make it possible to simply measure environmental allergens such as mites and pollens, and are useful for the prevention of various allergies and the like.

The invention claimed is:

1. A method for measuring an environmental biological allergen(s), characterized in that said method comprises the steps of immersing a test sample collected by using an adhesive sheet in a solution containing a substrate of a protease which said allergen(s) has(have), in the state of being adhered to said adhesive sheet without a pretreatment, said substrate' being Boc-Val-Leu-Lys-3RAX and/or Boc-amino acid-3RAX (wherein in these formulae, Boc represents t-butyloxycarbonyl group which is a protective group of amino group, and 3RAX represents methylene violet 3RAX); and detecting the protease activity in said test sample using a color change of said substrate solution as an indicator of the presence and/or quantity of the environmental biological allergen(s), thereby detecting said biological allergen(s), wherein said allergen(s) to be measured are at least one selected from the group consisting of mite and materials originating from mite.

2. The method according to claim 1, wherein the measurement is performed at room temperature.

3. The method according to claim 1 or 2, wherein said solution contains said substrate at a concentration of 5 μM to 20 μM.

4. The method according to claim 1 or 2, wherein said substrate is Boc-Val-Leu-Lys-3RAX.

5. The method according to claim 1, which measures at least one allergen obtained from the group consisting of floors, walls, windows, window frames, floor coverings, beddings, fiber products, furnitures, dust and/or house dust.

6. A method for measuring an environmental biological allergen(s) related to dust mites, characterized in that said method comprises the steps of:

immersing a test sample comprising dust collected by using an adhesive sheet in a solution containing a substrate of a protease of dust mites, in the state of being adhered to said adhesive sheet without a pretreatment, said substrate being Boc-Val-Leu-Lys-3RAX and/or Boc-amino acid-3RAX (wherein in these formulae, Boc represents t-butyloxycarbonyl group which is a protective group of amino group, and 3RAX represents methylene violet 3RAX); and detecting the protease activity in said test sample using a color change of said substrate solution as an indicator of the presence and/or quantity of the environmental biological allergen(s), thereby detecting said biological allergen(s).

7. The method according to claim 6, wherein the measurement is performed at room temperature.

8. The method according to claim 6, wherein said solution contains said substrate at a concentration of 5 μM to 20 μM.

9. The method according to claim 6, wherein said substrate is Boc-Val-Leu-Lys-3RAX.

10. The method according to claim 6, wherein said allegen (s) is/are collected from house dust.

11. The method according to claim 6, wherein said measuring step is performed by visually observing said color change.

12. The method according to claim 6, wherein said allergen is collected at a home and said measuring step is performed at said home.

* * * * *